United States Patent [19]

Reading et al.

[11] Patent Number: 5,346,306
[45] Date of Patent: * Sep. 13, 1994

[54] METHOD AND APPARATUS FOR MODULATED DIFFERENTIAL ANALYSIS

[75] Inventors: Michael Reading, London, England; Brian K. Hahn, Newark; Benjamin S. Crowe, Centerville, both of Del.

[73] Assignee: TA Instruments, Inc., New Castle, Del.

[*] Notice: The portion of the term of this patent subsequent to Jul. 6, 2010 has been disclaimed.

[21] Appl. No.: 60,214

[22] Filed: May 7, 1993

Related U.S. Application Data

[63] Continuation of Ser. No. 844,448, Mar. 2, 1992, Pat. No. 5,224,775.

[51] Int. Cl.$^5$ ............................................. G01N 25/00
[52] U.S. Cl. ........................................ 374/10; 374/33; 374/43
[58] Field of Search ..................... 374/10, 11, 12, 13, 374/14, 16, 31, 33, 43

[56] References Cited

U.S. PATENT DOCUMENTS

| | | |
|---|---|---|
| 2,975,629 | 3/1961 | Herbert . |
| 3,263,484 | 8/1966 | Watson et al. ........................ 374/11 |
| 3,271,996 | 9/1966 | Paulik et al. ......................... 374/10 |
| 3,339,398 | 9/1967 | Barrall et al. ........................ 374/11 |
| 3,360,993 | 1/1968 | MacMillan . |
| 3,417,604 | 12/1968 | Bean et al. ........................... 374/11 |
| 3,789,662 | 2/1974 | Zettler et al. . |
| 4,255,961 | 3/1981 | Biltonen et al. . |
| 4,350,446 | 9/1982 | Johnson . |
| 4,690,569 | 9/1987 | Veitch . |
| 4,747,698 | 5/1988 | Wickramasinghe et al. . |
| 4,783,174 | 11/1988 | Gmelin et al. ..................... 374/31 X |
| 4,812,051 | 3/1989 | Paulik et al. ......................... 374/10 |
| 4,838,706 | 6/1989 | Coey et al. ........................ 374/33 X |
| 4,840,496 | 6/1989 | Elleman et al. . |
| 5,046,858 | 9/1991 | Tucker . |
| 5,152,607 | 10/1992 | Ibar . |
| 5,224,775 | 7/1993 | Reading et al. ....................... 374/11 |

FOREIGN PATENT DOCUMENTS 0051266  5/1982  European Pat. Off. .
0380414  8/1990  European Pat. Off. .

OTHER PUBLICATIONS

S. G. Black and G. S. Dixon, "AC Calorimetry of Dimyristoylphosphatidylcholine Multilayers: Hysteresis and Annealing near the Gel to Liquid-Crystal Transition," Biochemistry, vol. 20, 1991, pp. 6740–6744.

G. S. Dixon, S. G. Black, C. T. Butler and A. K. Jain, "A Differential AC Calorimeter for Biophysical Studies," Analytical Biochemistry, vol. 121, 1982, pp. 55–61.

K. Drong, I. Lamprecht and Th. Plesser, "Calorimetric Measurements of an Intermittency Phenomenon in Oscillating Glycolysis in Cell–Free Extracts from Yeast," Thermochimica Acta, vol. 151, 1989, pp. 69–81.

V. V. Filimonov, S. A. Potekhin, S. V. Matveev and P. L. Privalov, "Thermodynamic Analysis of Scanning Microcalorimetric Data," Biophysical Chemistry, vol. 87, 1987, pp. 87–96.

O. L. Mayorga and E. Freire, "Dynamic analysis of differential scanning calorimetry data," Biophysical Chemistry, vol. 87, 1987, pp. 87–96.

(List continued on next page.)

Primary Examiner—William Cuchlinski, Jr.
Assistant Examiner—G. Bradley Bennett
Attorney, Agent, or Firm—Kirkland & Ellis

[57] ABSTRACT

The present invention relates to differential analytical techniques for determining the composition, phase, structure, identification or other properties of a material that undergoes a transition as function of a driving variable. As applied to differential scanning calorimetric analysis (DSC), the preferred embodiment comprises: (1) heating a sample of the material with a linear temperature ramp that is modulated with a sinusoidal heating rate oscillation; and (2) deconvoluting the resultant heat flow signal into rapidly reversible and non-rapidly reversible components.

44 Claims, 9 Drawing Sheets

OTHER PUBLICATIONS

R. Point, J. L. Petit and P. C. Gravelle, "Reconstruction of Thermokinetics From Calorimetric Data by Means of Numerical Inverse Filters," Journal of Thermal Analysis, vol. 17, 1979, pp. 383–393.

W. W. van Osdol, O. L. Mayorga and E. Freire, "Multifrequency calorimetry of the folding/unfolding transition of cytochrome c," Biophysical Journal, vol. 59, 1991, pp. 48–54.

J. Mitchell, "DSC: A New Design for Evaluating the Thermal Behavior of Materials," International Laboratory, Feb. 28, 1991, pp. 44–48.

E. Freire and R. L. Biltonen, "Statistical Mechanical Deconvolution of Thermal Transitions in Macromolecules. I. Theory and Application to Homogeneous Systems," Biopolymers, vol. 17, 463–479 (1978).

E. Freire, W. W. van Osdol, O. L. Mayorga and J. M. Sanchez-Ruiz, "Calorimetry Determined Dynamics of Complex Unfolding Transitions in Proteins," Annu. Rev. Biophys. Biophys. Chem. 1990. 19:159–88.

N. O. Birge and S. R. Nagel, "Specific-Heat Spectroscopy of the Glass Transition," Physical Review Letters, vol. 54, No. 25, Jun. 24, 1985, pp. 2674–2677.

N. O. Birge, "Specific-Heat Spectroscopy of Glycerol and Propylene Glycol Near the Glass Transition," Physical Review B., vol. 34, No. 3, Aug. 1, 1986, pp. 1631–1642.

N. O. Birge and S. R. Nagel, "Wide-Frequency Specific Heat Spectrometer," Rev. Sci. Instrum., vol. 58, Aug. 1987, pp. 1464–1470.

R. Garcia, "Scanning Tunneling Microscopy in Biology: Changing the Pace," Microscopy and Analysis, Jul. 1991, pp. 27–29.

J. E. Graebner, "Modulated-Bath Calorimetry," Review of Scientific Instruments, Jun. 1989, pp. 1123–1128.

I. Hatta and A. J. Ikushima, "Studies on Phase Transitions by AC Calorimetry," Japanese Journal of Applied Physics, Nov. 1981, pp. 1995–2011.

M. Heitschold, P. K. Hansma, A. L. Weisenhorn, "Scanning-Probe-Microscopy and Spectroscopy in Materials Science," Microscopy and Analysis, Sep. 1991, pp. 25–27.

D. H. Jung, T. W. Kwon, D. J. Bae, I. K. Moon and Y. H. Jeong, "Fully Automated Dynamic Calorimeter," Meas. Sci. Technol., vol. 3, 1992, pp. 475–484.

S. MacPherson, "Atomic Resolution", Laboratory News, Mar. 19, 1990.

O. L. Mayorga, W. W. van Osdol, J. L. LaComba and E. Freire, "Frequency Spectrum of Enthalpy Fluctuations Associated with Macromolecular Transitions," Proc. Natl. Acad. Sci. U.S.A., vol. 85, Dec. 1988, pp. 9514–9518.

M. J. Miles, "The Application of STM/AFM to Biological Molecules," Microscopy and Analysis, Jul. 1990, pp. 7–9.

H. S. Rade and F. Ringelmann, "Wechselstromkalorimetrie-Ein Empfindliches und Kontinuirlich Registrierendes Verfahren Zur Messung Spezifischer Warmen Kleiner Proben," Feinwerktechnik & Messtechnik, Jul. 1977, pp. 223–226.

A. Rosenowaig, "Photoacoustic Microscopy," International Laboratory, Sep./Oct. 1979, pp. 37–43.

P. F. Sullivan and G. Seidel, "Steady-State, AC-Temperature Calorimetry," Physical Review, vol. 173, No. 3, Sep. 15, 1968, pp. 679–685.

N. F. van Hulst and F. B. Segerink, "Optical Microscopy Beyond the Diffraction Limit," Microscopy and Analysis, Jun. 1992, pp. 21–23.

C. C. Williams and H. K. Wickramasinghe, "Photothermal Imaging with Sub-100-nm Spatial Resolution," Photoacoustic and Photothermal Phenomena Proceedings, pp. 364–368.

H. Yao and I. Hatta, "An AC Microcalorimetric Method for Precise Heat Capacity Measurement in a Small Amount of Liquid," Japanese Journal of Applied Physics, Jan. 1988, pp. 121–122.

Ulvac Sinku-Riko, Inc. product brochure ACC-1, "AC Calorimeter," publication date unknown, Catalog No. 8909-A13E/90.71000.

Ulvac Sinku-Riko, Inc. product brochure, "Thermal Constants Analyzer by AC Calorimetric Method," publication date unknown, Catalog No. 9010-P1TR1/90.10,3000.

Ulvac Sinku-Riko, Inc. product brochure ACC-VL1, "AC Calorimeter," publication date unknown, Catalog No. 9102-A24E.

Microscopy and Analysis, "Aris Scanning Tunneling Microscope," Jan. 1992.

Di product brochure, "Nanoscope II, Scanning Tunneling Microscope," publication date unknown.

Struers product brochure, "Welcome to the World of Atoms, Tunnelscope 2400," publication date unknown.

Struers product brochure, "Welcome to the World of Atoms, Tunnelscope 2400, Software Version 2.0," publication date unknown.

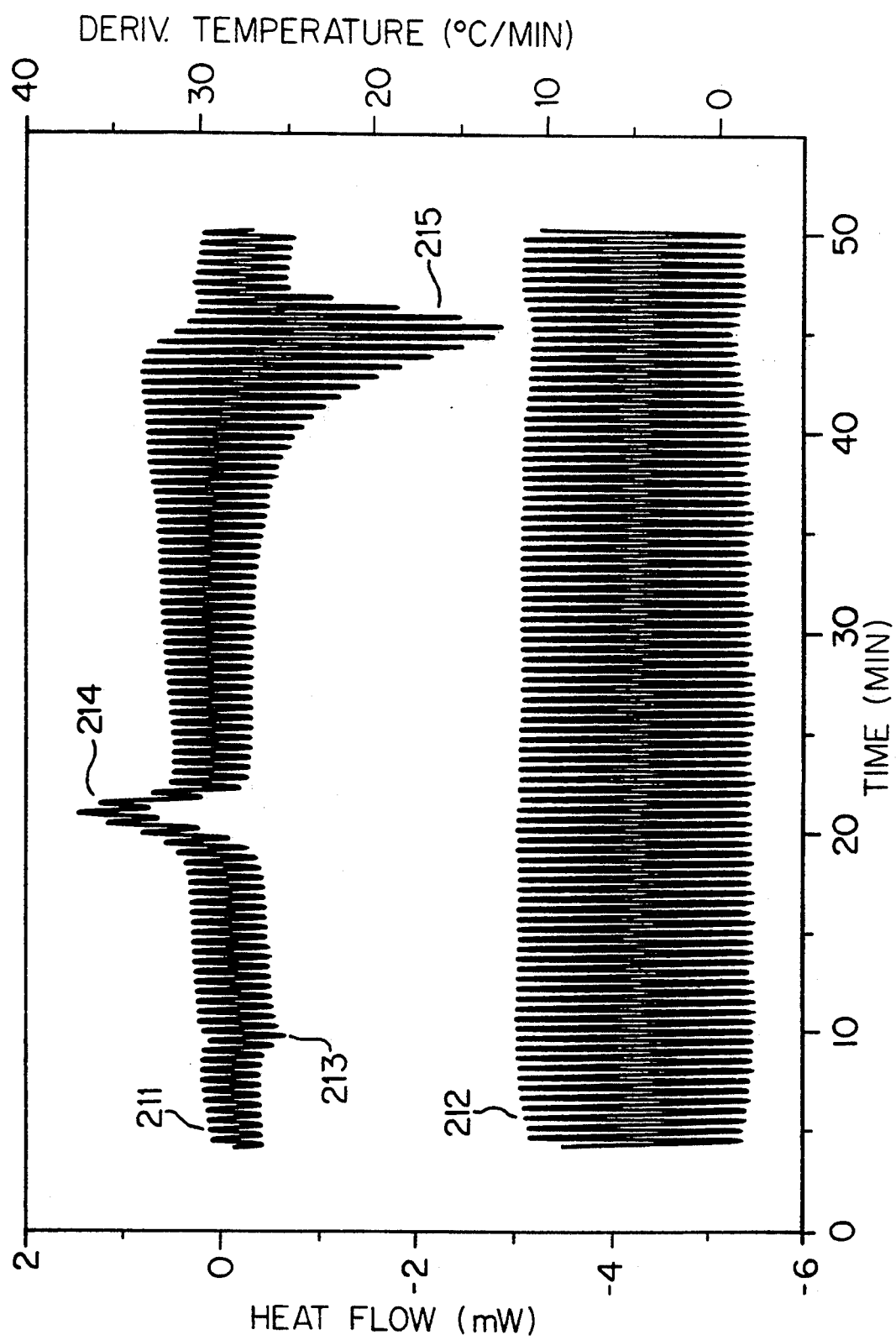

METHOD AND APPARATUS FOR MODULATED DIFFERENTIAL ANALYSIS

This application is a continuation of U.S. patent application Ser. No. 07/844,448, now U.S. Pat. No. 5,224,775, filed Mar. 2, 1992.

BACKGROUND

1. Field of the Invention

The present invention relates to differential analytical techniques for determining the composition, phase, structure, or other properties of a sample of material.

2. Background of the Invention

Thermal analysis techniques generally comprise measuring a physical parameter as a function of the temperature of the sample. The sample temperature is strictly controlled throughout the analysis. Whenever the sample undergoes a chemical transformation, a physical transformation, a phase change or another transition which affects the physical parameter being measured, the changes in that physical parameter may be interpreted to analyze the composition, structure, or thermal stability of the sample.

In differential thermal analysis techniques, the physical parameter of the sample being measured is compared to that of a reference, as a function of the temperature of the sample. The difference in the physical parameter measured for the sample and that measured for the reference is then recorded. The differential thermal analysis technique compensates for the effects of heating rate and ambient conditions that could cause changes in the measured physical parameter of the sample and reference. The differential thermal analysis technique can increase the sensitivity of the measurement of the physical parameter by removing large offsets in the value of the physical parameter whenever the precision of the measuring apparatus is limited.

One common thermal analysis technique is Differential Scanning Calorimetry (DSC). DSC is a thermal analysis technique which measures the temperatures and heat flow associated with chemical or physical transitions in materials as a function of time and temperature. The classical DSC method comprises heating the sample material and the reference material at a constant rate of temperature increase, typically 5° C. to 20° C. per minute, and recording the difference in heat flow into or out of the sample and the reference as a function of temperature.

Other differential thermal analysis techniques include Pressure Differential Scanning Calorimetry (PDSC), Differential Thermal Analysis (DTA), Pressure Differential Thermal Analysis (PDTA), Differential Photocalorimetry (DPC), pressure Differential Photocalorimetry (PDPC), Differential Thermogravimetry (DTG), and Pressure Differential Thermogravimetry (PDTG).

Furthermore, the present invention applies to all differential analysis techniques. It is not limited to differential thermal techniques. Whereas thermal differential analysis techniques depend upon temperature as the driving variable, non-thermal differential analysis techniques depend upon another driving variable, such as pressure, applied stress, or wavelength of incident radiation.

DSC measurements provide quantitative and qualitative information about the sample transitions that involve endothermic or exothermic processes, or changes in heat capacity. Pressure DSC is a related technique in which the heat flow and temperature of transitions are measured as a function of temperature under controlled pressure, or as a function of pressure under controlled temperature.

Differential Thermal Analysis, like DSC, measures the temperatures and heat flow associated with transitions in materials as a function of time and temperature. However, unlike DSC, DTA results are semi-quantitative. Pressure DTA is a related technique in which the heat flow and temperature of transitions are measured as a function of temperature under controlled pressure, or as a function of pressure under controlled temperature. DTA is generally carried out at higher temperatures than DSC.

Differential Photocalorimetry measures the heat absorbed or released by a sample as it and a reference are exposed simultaneously to radiation of known wavelength and intensity. Pressure DPC is a related technique in which the heat absorbed or released by the sample is measured as a function of temperature under controlled pressure, or as a function of pressure under controlled temperature.

Differential Thermogravimetry measures the differential weight change of a sample and a reference as a function of time and temperature. Pressure DTG is a related technique in which the differential weight change is measured as a function of temperature under controlled pressure, or as a function of pressure under controlled temperature.

High resolution analytical techniques are described in U.S. patent application Ser. No. 07/638,847. That application is incorporated by reference herein. Those techniques seek to improve the resolution of changes in a characterizing physical parameter by controlling the rate of sample heating during transitions as a function of the rate of change of the physical parameter. When non-differential thermal analysis techniques are used, the high resolution techniques are effective in improving resolution for many transitions. However, they usually reduce the sensitivity of transitions when applied to differential thermal analysis techniques. This is because, for most differential thermal analysis techniques, the magnitude of the differential physical parameter is a direct function of the heating rate. Reducing the heating rate during transitions causes the differential signal to change, which may alter or obscure the true differential signal resulting from the transition event. This obscuring of the physical parameter can reduce the utility of the high resolution techniques when applied to conventional differential thermal analysis techniques.

Conventional differential thermal analysis techniques are limited in their ability to separate non-reversible events caused by enthalpic processes (chemical or physical) from reversible events such as changes in the heat capacity of the sample. This is because the reversible and non-reversible processes often occur simultaneously, or occur severely overlapped in time and/or temperature.

In addition, conventional and high resolution thermal analysis techniques cannot distinguish between rapidly reversible and non-rapidly reversible transitions within a single heating or cooling scan of the sample.

DEFINITIONS

"Transition" or "Transformation", as used herein, mean any type of physical or chemical transformation, phase change, or structural change in a material.

"Analyzing", as used herein with respect to materials, means determining the composition, phase, structure, and/or identification of the material.

"Driving variable", as used herein, means the independent physical parameter, such as temperature, pressure, applied stress, or wavelength of incident radiation, that is being used to drive a material through a transition. For example, in thermal analysis techniques such as DSC, temperature is typically the driving variable.

"Characterizing differential physical parameter", as used herein, means the dependent differential physical parameter characterizing the sample, such as its heat flow, weight change, or change in dielectric or mechanical properties.

"Rapidly reversible", as used herein, means any portion of a signal, transition, or event which is a direct function of the rate of change of the driving variable. For example, the contribution to the heat flow signal in DSC attributable to the rate of change of temperature of the sample material is a rapidly reversible transition. In DSC, for example, one of the contributions to the rapidly reversible portion of the heat flow signal is the heat capacity of the sample material. Rapidly reversible processes include those processes which are thermodynamically reversible and can occur rapidly relative to the rate of change of the driving variable.

"Non-rapidly reversible", as used herein, means any portion of a signal, transition or event which is a direct function of the value of the driving variable. For example, the contribution to the heat flow signal in DSC attributable to the absolute temperature of the sample material is a non-rapidly reversible transition. This might be caused by a chemical or physical change taking place such as recrystallization. Non-rapidly reversible processes include those processes which are thermodynamically irreversible, as well as processes which are thermodynamically reversible, but which reverse very slowly relative to the rate of change of the driving variable due to the kinetic limitations of the process.

"Deconvolution", as used herein, means the process of separating the dependence of a characterizing physical parameter on a driving variable into two or more component parts so that the component parts can be utilized or analyzed separately, or compared with each other. For example, the dependence of a characterizing physical parameter can be deconvoluted into rapidly reversible and non-rapidly reversible components.

"Signal baseline", as used herein, means that portion of a signal representing the value of a characterizing physical parameter obtained in a range in which there are no transitions or transformations.

"Sensitivity" of an analytical technique, as used herein, means the degree to which signals associated with transitions can be physically distinguished from the signal baseline in the analytical data produced by the technique. This quality of the analytical technique is most critical when the value of the driving variable is changing very slowly.

"Resolution" of an analytical technique, as used herein, means the degree to which signals associated with different transitions can be physically separated in the analytical data produced by the technique. This quality of the analytical technique is most critical when multiple transitions occur at closely spaced values of the driving variable.

"Moving averaged", is a data smoothing technique that can be applied to data collected as discrete data points at uniform increments, comprising averaging the raw data over a window of n data points to obtain a single smoothed data point, incrementing the window by one data point, and repeating the process until all the data has been averaged. Thus the first n raw data points, data points i=1, ... n, are averaged to calculate the first smoothed data point, data points i=2, ... n+1, are averaged to produce the second data point, etc.

A "pulse wave" is a wave of spikes or impulse functions occurring at regular intervals. As applied to thermal analysis techniques, a pulse wave could be produced by bursts of instantaneous energy, e.g., from a laser, at regular intervals. The key characteristic of a pulse wave is that the duration of the energy burst is short compared to the duration of its effect.

SUMMARY OF THE INVENTION

In modulated DSC (MDSC), a rapid heating rate oscillation is added to a conventional linear temperature ramp. If the heating rate oscillation has low amplitude but high frequency then it is possible to obtain a relatively high instantaneous heating rate even though the underlying heating rate is comparatively low.

The present invention uses a computer system to control a differential thermal analytical technique by monitoring and modulating the technique's driving variable and deconvoluting a resultant characterizing differential physical parameter into rapidly reversible and non-rapidly reversible contributions.

For example, when the analytical technique is DSC, the driving variable is temperature and the characterizing differential physical parameter is heat flow. The response of the calorimeter to the sample can be expressed as follows:

$$dQ/dt = dT/dt * f_r(t,T) + f_n(t,T) \qquad (1)$$

Where
 $dQ/dt$ = heat flow out of the sample (Joules/sec)
 $dT/dt$ = heating rate (° C./sec)
 $t$ = time (seconds)
 $T$ = temperature (° C.)
 $f_r(t,T)$ = rapidly reversible contribution (Joules/° C.)
 $f_n(t,T)$ = non-rapidly reversible contribution (Joules/sec)

$f_r(t,T)$ and $f_n(t,T)$ are functions of time and temperature derived by deconvolution of the analytical data.

This equation separates the DSC differential heat flow into a rapidly reversible portion, $f_r(t,T)$, which is dependent on heating rate, and a non-rapidly reversible portion, $f_n(t,T)$, which is not dependent on heating rate.

The modulated DSC heat flow signal will contain a heat flow oscillation which will be to some degree out of phase with the heating rate oscillation. The modulated DSC heat flow signal can be deconvoluted to separate the rapidly reversible, $f_r(t,T)$ and non-rapidly reversible, $f_n(t,T)$, heat flow contributions, as shown in equation (1).

Deconvolution of the modulated DSC heat flow and temperature data into parameters other than the ones described above is also possible. For example, the modulated heat flow and temperature data could be deconvoluted to derive direct kinetic information about the sample, such as its reaction rate and activation energy.

Other useful properties which could be deconvoluted include the heat capacity of the sample and the phase shift between the modulated sample heating rate and the resultant heat flow.

The modulated DSC technique can be further extended to automatically or manually vary the modulation frequency and/or amplitude during the DSC scan so as to obtain data at multiple frequencies, amplitudes and temperatures during a single heating or cooling scan. This can be accomplished by applying modulation cycles of specific frequencies, or by combining a plurality of frequencies into each modulation cycle and deconvoluting the frequency information along with the characterizing physical parameters. This scanning MDSC technique has the advantages of improving the productivity of the analytical laboratory and reducing the environmental-and-operator-related variations in multiple sample runs. As a further extension, the deconvolution process could be coupled with frequency and/or amplitude selection to enable frequency/amplitude optimization for specific parameter values or sample conditions.

A major advantage of modulated DSC is the ability to use DSC to separately measure and study rapidly reversible and non-rapidly reversible events which are overlapped in temperature and time. For example, in polymer chemistry, it is common for a non-enthalpic event, such as a change in heat capacity due to a glass transition, to occur at the same temperature as an enthalpic event, such as a recrystallization. When these temperature-overlapped events are studied with conventional DSC, the resultant heat flow contributions from each event are additive and therefore obscure each other. When the modulated DSC technique is used to analyze such a sample, the resultant heat flow signal can be deconvoluted into rapidly reversible and non-rapidly reversible signals corresponding to the glass transition and recrystallization events respectively.

A second major advantage of modulated DSC is the ability to use variable heating rate DSC techniques, termed Controlled-Rate or Constrained-Rate DSC, to reduce the underlying heating rate of the DSC scan during transitions in order to improve resolution, without a resultant loss in DSC sensitivity. In the Controlled-Rate DSC case, the heat flow signals are measured in Joules/° C. instead of the conventional Joules/sec, thereby removing the dependency on heating rate and the resultant reduction in signal magnitude at low heating rates.

Another advantage of modulated DSC is an improved ability to study the kinetic properties of chemical reactions with respect to temperature. For a given modulation frequency and amplitude, the ratio of the rapidly reversible component of the heat flow to the non-rapidly reversible component is directly related to the kinetic rates of the forward and reverse reactions of the sample material at the measurement temperature. Reactions which are overlapped in temperature but have different rates of reaction can be separated into rapidly reversible and non-rapidly reversible components by appropriate adjustment of the modulation frequency and amplitude.

A first object of the present invention is to provide a method for controlling the driving variable in differential analysis techniques to substantially improve the resolution of transitions through the use of variable rates of change in the driving variable.

A second object of the present invention is to provide a temperature control method for differential thermal analysis techniques which achieves substantially improved resolution of transitions through the use of variable heating rate heating techniques.

A third object of the present invention is to separate the characterizing differential physical parameter into rapidly reversible and non-rapidly reversible components.

A fourth object of the present invention is to provide the analyst with a method of adjusting the amount of separation between rapidly reversible and non-rapidly reversible transitions.

A fifth object of the present invention is to improve the sensitivity of differential analysis techniques.

A sixth object of the present invention is to provide the analyst with an alternate method for studying the kinetic properties of chemical reactions.

A seventh object of the present invention is to obtain more accurate transition temperatures.

An eighth object of the present invention is to simplify the interpretation of differential thermal analysis data by more sharply defining the temperatures at which transitions occur.

A ninth object of the present invention is to isolate signal changes so that they can be more easily measured, integrated, compared with other results, and interpreted.

These and other objects of the present invention are described in greater detail in the following description of the invention, the appended drawings and the attached claims.

DESCRIPTION OF THE DRAWINGS

FIGS. 2a–2c are DSC scans of Poly(ethyleneterephthalate) (PET) obtained according to the methods described in Example 2.

DESCRIPTION OF THE PREFERRED EMBODIMENT OF THE INVENTION

The present invention resides in control methods for conventional differential analytical apparatus, and is an improvement on the methods currently practiced to control such conventional differential analytical apparatus.

The following detailed description of the present invention applies specifically to differential scanning calorimetry, in which temperature is the driving variable and heat flow is the characterizing differential physical parameter. However, although the present invention is described as applied to differential scanning calorimetric analysis, it should be understood that the present invention could be used with any differential thermal analysis method including Pressure Differential Scanning Calorimetry, Differential Thermal Analysis, Pressure Differential Thermal Analysis, Differential Photocalorimetry, Pressure Differential Photocalorimetry, Differential Thermogravimetry, and Pressure Differential Thermogravimetry, as well as any combination of these techniques. The principles and methods described herein with reference to differential scanning calorimetric analysis could be applied to any and all of the thermal analytical methods listed above, as well as to other analytical methods wherein a characterizing differential physical parameter is measured as a function of a driving variable.

Figure 1A:
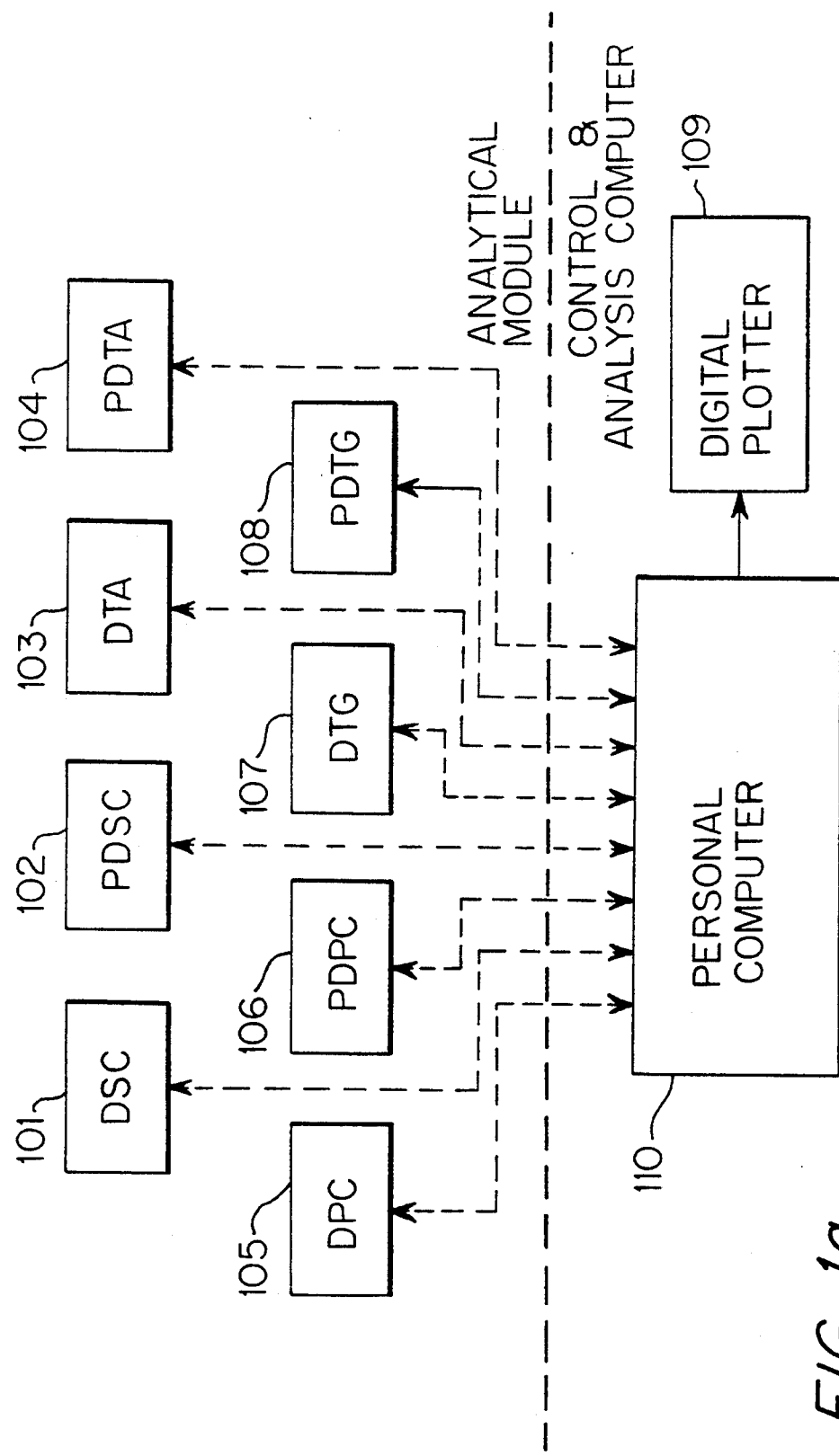
FIG. 1a is a block diagram showing how different differential thermal analysis techniques may be used with the present invention.

FIG. 1a is a schematic representation of the present invention as it may be used with Differential Scanning Calorimetry (DSC) 101, Pressure Differential Scanning Calorimetry (PDSC) 102, Differential Thermal Analysis (DTA) 103, Pressure Differential Thermal Analysis (PDTA) 104, Differential Photo-calorimetry (DPC) 105, Pressure Differential Photocalorimetry (PDPC) 106, Differential Thermogravimetry (DTG) 107, Pressure Differential Thermogravimetry (PDTG) 108, digital plotter 109 and personal computer 110.

Figure 1B:
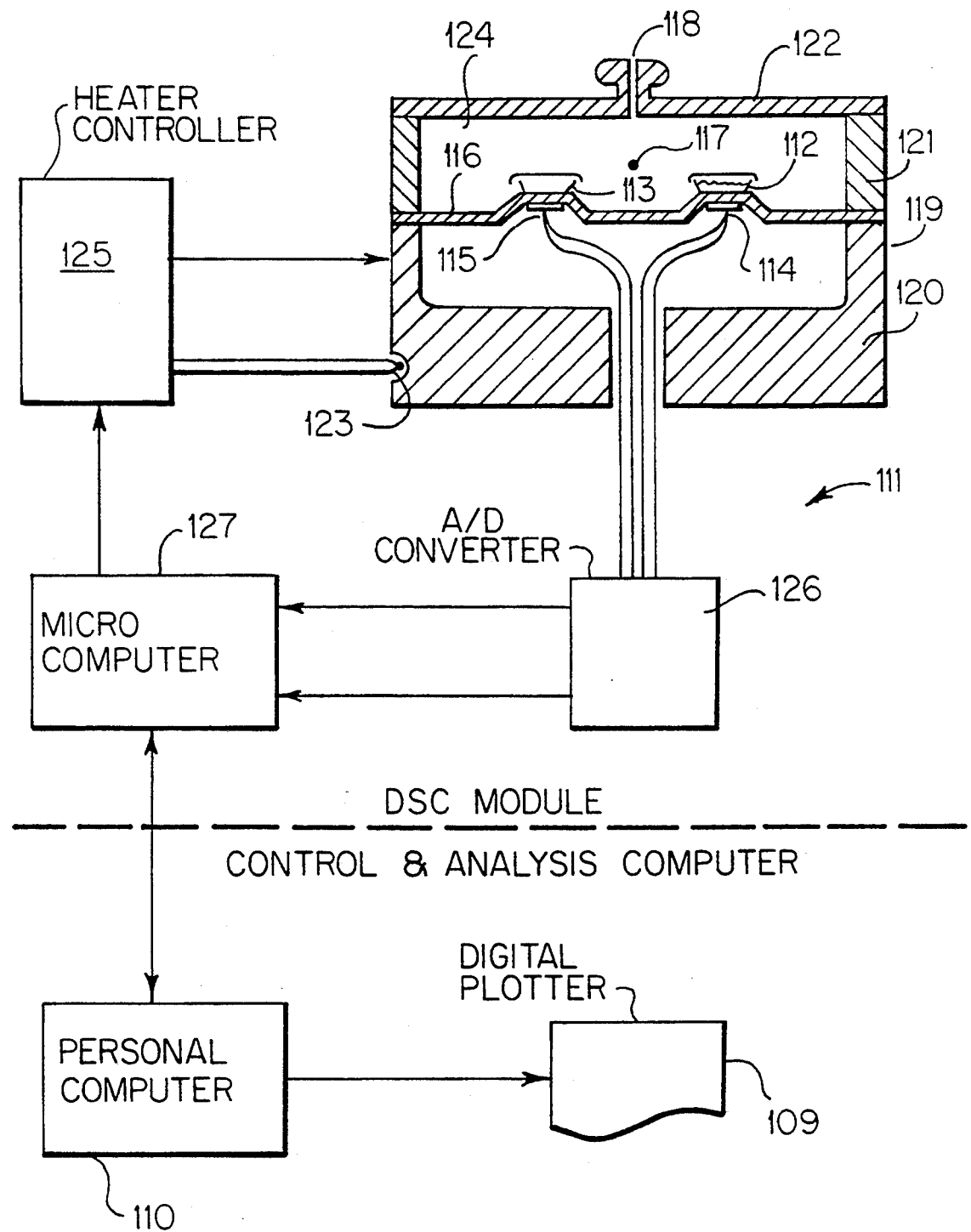
FIG. 1b is a block diagram of a differential scanning calorimetric apparatus.

FIG. 1b is a schematic representation of a conventional differential scanning calorimeter 111 comprising: a sample pan 112; reference pan 113; sample temperature thermocouple 114; reference temperature thermocouple 115; thermoelectric disc 116; purge gas inlet 117; purge gas outlet 118; electric furnace 119 comprising silver block heater 120, silver ring 121, silver lid 122, and heater thermocouple 123; furnace chamber 124; heater controller 125; analog-to-digital converter 126; and microcomputer 127. FIG. 1b also shows personal computer 110 and digital plotter 109. The differential scanning calorimeter measures the heat flow difference between sample pan 112 and reference pan 113 which are supported by a thermoelectric disc 116 inside a closed furnace chamber 124. The thermoelectric disc 116 serves as the major heat flow path for transferring heat from furnace 119 to sample pan 112 and reference pan 113. The disc is also used as a common material of the differential thermocouple for measuring the temperature difference between the sample and reference pans. Microcomputer 127 receives differential temperature and sample temperature from sample thermocouple 114 and reference thermocouple 115 via analog-to-digital converter 126. Microcomputer 127 also controls the temperature of the furnace 119 by controlling the power to the furnace using heater controller 125. In the preferred embodiment of the present invention, the temperature of the furnace is controlled by the microcomputer in accordance with the steps outlined below. However, the present invention can be practiced using any combination of computers, hardware and operator control. Personal computer 110 and digital plotter 109 are used to analyze, store, display and plot the analytical results. A purge gas is usually introduced via the purge gas inlet 117. The purge gas can be a gas that reacts with constituents of the sample being analyzed, or it can be an inert gas, i.e., a gas that does not react with the sample used to prevent reactions with air. Typical purge gases include dry air, oxygen, nitrogen, argon, helium, carbon monoxide and carbon dioxide.

The preferred embodiment of the present invention is outlined below as applied to differential scanning calorimetric analysis. The linear heating rate is modulated at a predetermined frequency and amplitude such that the maximum heating rate obtained during each modulation period is substantially larger than the underlying linear ramp rate, but the total sample temperature excursion during each modulation period is relatively small.

The larger the difference between the maximum heating rate and the underlying rate, the greater will be the resultant sensitivity of the technique. The preferred maximum heating rate is at least twice the underlying heating rate. A larger heat sinking capacity in the system will improve modulation performance. To this end, a cooling jacket or integral cooling system is desirable.

The smaller the sample temperature excursion during each modulation period, the greater will be the resultant resolution of the technique. A temperature excursion less than 2° C. is preferred.

The modulation frequency is selected to produce the desired separation between rapidly reversible and non-rapidly reversible components of the heat flow signal. For thermodynamically reversible processes, the higher the modulation frequency, the greater the amount of signal that will deconvolute as non-rapidly reversible and the smaller the amount that will deconvolute as rapidly reversible. Lower modulation frequencies cause the opposite effect.

The sample temperature and differential heat flow resulting from the modulation is stored and analyzed over one full modulation period using a moving deconvolution technique which separates the A/C and D/C components of the heat flow. These separated components are moving-averaged over one full modulation cycle and reported in terms of the underlying heating rate. The separated components are summed to produce the resultant total heat flow at the underlying rate.

The preferred embodiment comprises the following steps:

STEP 1. Selecting an underlying heating rate.
STEP 2. Selecting a modulation frequency.
STEP 3. Selecting a modulation amplitude.
STEP 4. Applying a sinusoidal modulation to the heating rate selected in step 1, at the frequency selected in step 2 and at the amplitude selected in Step 3.
STEP 5. Monitoring the sample temperature.
STEP 6. Monitoring the differential heat flow.
STEP 7. Deconvoluting the sample temperature and differential heat flow into rapidly reversible and non-rapidly reversible components of heat flow.
STEP 8. Combining the rapidly reversible and non-rapidly reversible components of heat flow to construct the total heat flow at the underlying heating rate.

The present invention can be practiced using any applicable deconvolution technique to separate the rapidly reversible and non-rapidly reversible components of the measured heat flow. In the preferred embodiment, a discrete differential Fourier transform (DFT) technique was used to deconvolute the modulated DSC sample temperature and heat flow. The discrete Fourier transform algorithm for deconvoluting the sample temperature and differential heat flow into rapidly reversible and non-rapidly reversible components of heat flow (step 7 of the preferred embodiment of the current invention) comprises the following substeps:

SUBSTEP 7-1. Calculating the D/C component of the modulated temperature and heat flow signals. The D/C component of each signal is calculated as the unweighted moving average of the signal over one or more full modulation periods. This moving average is the D/C value for the central point in the average.
SUBSTEP 7-2. Calculating the A/C component of the modulated temperature and heat flow signals. The A/C component of each signal is calculated as a point-by-point subtraction of the D/C component, calculated in substep 7-1, from the modulated signal.
SUBSTEP 7-3. Correlating the A/C component of the modulated temperature and heat flow signals with the sinusoidal modulation. The A/C component of each signal is correlated with the modulation signal by multiplying the signal by an in-phase sinusoidal signal (cosine) and 90 degree out-of-phase sinusoidal signal (sine), with the same period as the modulation. The sine and cosine products are summed over one or more full modulation periods. These sums are calculated for each successive point in the modulated temperature and heat flow signals.

SUBSTEP 7-4. Calculating the A/C amplitude and phase of the modulated temperature and heat flow signals. The A/C amplitude of each signal is calculated by taking the square root of the sum of the squares of the sine and cosine sums from substep 7-3. The phase shift of each signal is calculated by taking the arctangent of the ratio of the sine and cosine sums calculated in substep 7-3.

SUBSTEP 7-5. Smoothing the amplitude and phase signals. The amplitude and phase signals are smoothed with an unweighted moving average over one or more complete modulation periods.

SUBSTEP 7-6. Calculating the rapidly reversible coefficient. The coefficient for the rapidly reversible component, $f_r(T,t)$, is calculated by dividing the A/C amplitude of the heat flow by $2\pi f A_T$, where f is the modulation frequency and $A_T$ is the A/C amplitude of the temperature.

SUBSTEP 7-7. Calculating the rapidly reversible component. The rapidly reversible component is calculated by multiplying the rapidly reversible coefficient by the underlying heating rate.

SUBSTEP 7-8. Calculating the non-rapidly reversible component. The non-rapidly reversible component is calculated by subtracting the rapidly reversible component from the D/C heat flow signal from substep 7-1.

Deconvolution and fitting techniques that may be used to implement the present invention are described in *Numerical Recipes, The Art of Scientific Computing*, by W. H. Press, B. P. Flannery, S. A. Teukolsky and W. T. Vetterling (Cambridge University Press, New York, 1986), which is hereby incorporated by reference. Chapter 12, page 401, describes a Fast Sine and Cosine Transform technique that is somewhat similar to the DFT deconvolution described above. Chapter 14, page 515, "Singular Value Decomposition", and page 523, "Levenberg-Marquardt Method," describe fitting techniques that have been successfully used with the present invention.

Techniques other than the ones discussed above may be used to deconvolute the heat flow into rapidly reversible and non-rapidly reversible portions. Physical characterizing parameters, other than those described above, may also be deconvoluted for report generation and/or control of the DSC module, or for other downstream uses.

The present invention can be further enhanced by using variable heating rate techniques, as described, for example, in U.S. patent application Ser. No. 07/638,847 to reduce the underlying heating rate during transitions thereby improving the resolution, without sacrificing the sensitivity of the heat flow measurement.

The present invention can also be applied to chemical or physical transformations that occur upon cooling as well as upon heating, or upon any combination of heating and cooling cycles, whether or not separated by constant temperature periods or constant-rate heating or cooling periods. When the technique is used to analyze materials that undergo transitions upon cooling, the methods described above are still applied, but with the sample cooling rate substituted for the sample heating rate, and with a cooling apparatus substituted for or used in conjunction with the furnace. The present invention applies equally well to modulation of a cooling system, in which a cold sink (heat source) works with a modulated cooling device, or a combination of modulated heating and modulated cooling.

The sample could be heated or cooled using hot or cold air, lasers, fluid baths, microwave energy, chemical reactions, or other appropriate heating or cooling techniques.

The preferred embodiment of the present invention, as described above, controls the heating rate of the furnace. However, the present invention could be practiced by controlling the heating rate of the sample, or by controlling the sample temperature itself instead of by controlling the heating rate.

DESCRIPTION OF FURTHER EMBODIMENTS OF THE INVENTION

The present invention may be implemented using a modulation wave shape other than a sine wave. In particular, a square wave, sawtooth wave, triangular wave, pulse wave, or any applicable polynomial wave, or combination of waves, whether symmetric or not, may be used. The modulation wave must be a periodic wave if the discrete Fourier transform deconvolution method, described above, is to be used.

The present invention may also be implemented using deconvolution techniques and discrimination criteria other than a discrete Fourier transform and heating rate, respectively. In particular, the deconvolution may be performed by fitting the data to an appropriate mathematical function, by comparing the data to a data base or library of known results, or by solving systems of simultaneous equations that describe the data.

The present invention may also be implemented with or without deconvolution of the data. Any deconvolution performed may be done in real-time or as post-processing of the data.

The present invention may also be implemented using hardware, software, or a combination of hardware and software. For example, the heating rate may be modulated by adjusting the physical characteristics of the furnace or cooling system, or by programming a computer that controls the furnace or cooling system heating rate. Analog devices such as amplifiers could be used for multiplication, integrators for summation, inverters for subtraction, and comparators for decision-making.

The present invention may be implemented on a system employing a technique simultaneous with DSC or DTA. For example, on a simultaneous TGA/DTA system.

The present invention may also be implemented on a system employing an automatic loading and/or unloading apparatus, or automatic heating rate, frequency and/or amplitude adjustment between experiments or heating/cooling cycles. For example, the present invention may be implemented on a robotic sample changing system with preprogrammed experimental parameters for each sample. Alternately, a computer may be used to determine the appropriate adjustments to the heating rate, the modulation frequency and/or amplitude for one experiment, based upon the results of a previous experiment.

The following examples are provided to illustrate certain embodiments of the present invention. They are not to be construed as limiting the invention in any way.

EXAMPLE 1: DIFFERENTIAL SCANNING CALORIMETRIC ANALYSIS

This example describes the experimental apparatus and procedures used in Examples 2–4. The DSC system used for these analyses was the TA Instruments DSC 2910 Differential Scanning Calorimeter connected to the TA Instruments Thermal Analyst 2100 computer/thermal analyzer. The instruction manuals for this apparatus are hereby incorporated by reference. All samples used in the experiments were readily available commercial products. Sample sizes varied from 4.45 to 5.1 milligrams of material. The samples were loaded into standard aluminum DSC sample pans with crimped aluminum lids. The purge gas used was nitrogen (99.998% pure). The DSC was set up and leveled on a solid non-vibrating work surface.

Before operation of the DSC apparatus, a steady flow of purge gas was established. The purge gas was connected through a pressure regulator and flow meter to the purge inlet port on the instrument. The flow meter was adjusted to a flow rate of 50 ml/minute purge flow rate over the sample and reference pans.

The DSC cell was cleaned and calibrated according to the instructions in the DSC 2910 Users Manual.

The sample material was weighed on an analytical balance, and placed in the DSC sample pan with a crimped lid. The sample pan was then placed in the DSC cell on the sample platform. A matching empty DSC sample pan with crimped lid was placed on the reference platform. The DSC cell was then closed using the silver lid. The stainless steel lid and bell jar were then applied to the cell if the scan was to be a conventional DSC scan or if the sample was being heated prior to quenching. In other cases, a standard DSC cooling can, without coolant, was applied to the cell, to provide heat sinking during heating rate modulation.

Sample identification, sample weight, the desired underlying heating rate, the starting temperature, the final temperature to be reached, and the modulation frequency and amplitude were programmed into the computer/thermal analyzer.

The DSC experimental sequence was started by pressing the "Start" button on the DSC 2910. The computer/thermal analyzer then automatically heated the sample according to the present invention, as described specifically in Examples 2–4, while deconvoluting and recording the sample temperature, differential heat flow, rapidly reversible component and non-rapidly reversible component of the heat flow using the DFT technique, until the specified final temperature was reached. The furnace then returned to ambient temperature and the sample was unloaded manually.

EXAMPLE 2: COMPARISON OF DSC SCANS OF POLY(ETHYLENE TEREPHTHALATE) BY CONVENTIONAL AND MODULATED DSC

Figure 2A:
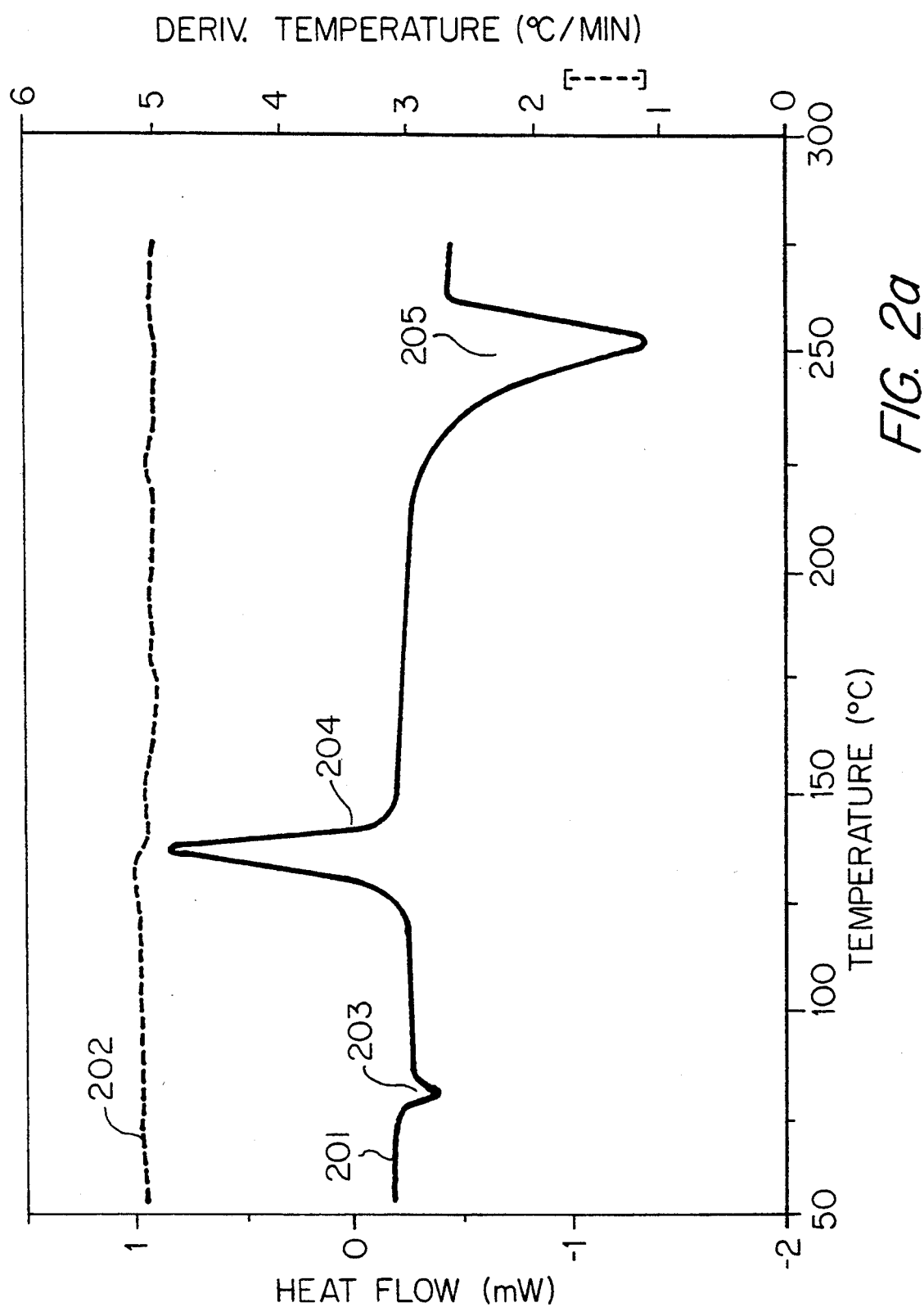
Figure 2C:
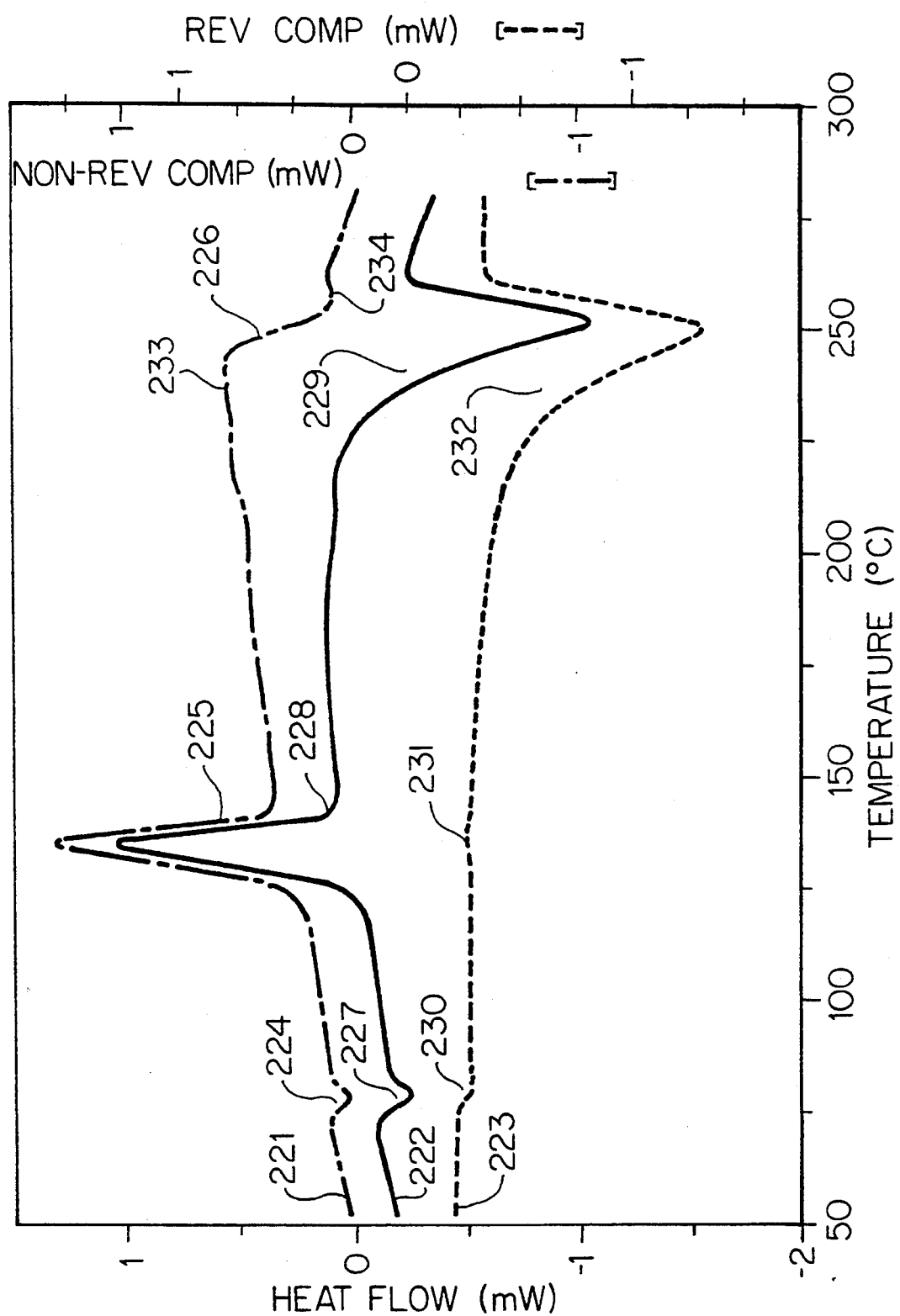

A 4.45 milligram sample of quenched Poly(ethylene terephthalate) (PET) was examined by conventional DSC and the method of the preferred embodiment of the present invention to compare the results obtained by each method. The experimental procedures followed in this example for setting up the apparatus, weighing the samples, loading the samples, and running the analyses were described in Example 1. The sample was conditioned prior to each run by heating the sample to 300° C. in the DSC cell; removing the sample from the DSC cell and immediately quench-cooling it to 0° C. by placing the sample pan on a block of ice for 5 seconds; reheating the sample in the DSC cell to 90° C.; and cooling the sample at 1° C./minute to ambient temperature. The results of the analyses are shown in FIGS. 2a–2c. FIG. 2a is a DSC scan obtained according to the conventional method, at a constant heating rate of 5° C./minute from ambient temperature to 300° C. FIGS. 2b and 2c are DSC scans obtained according to the preferred embodiment (steps 1–8) of the present invention, at an underlying heating rate of 5° C./minute from ambient temperature to 300° C., using a modulation frequency of 2 cycles/minute and a modulation amplitude of +/−7.5 ° C./minute.

Each of the scans shows several curves. Curve 201 (FIG. 2a) is a plot of the differential heat flow of the sample as a function of sample temperature. Curve 202 (FIG. 2a) is a plot of the derivative with respect to time of the sample temperature versus sample temperature. Curve 211 (FIG. 2b) is a plot of the differential heat flow of the sample as a function of time. Curve 212 (FIG. 2b) is a plot of the derivative with respect to time of the sample temperature versus time. The curves in FIG. 2c show the results of deconvoluting the heat flow and temperature data of FIG. 2b using the deconvolution algorithms of the preferred embodiment of the present invention. Curve 221 (FIG. 2c) is a plot of the non-rapidly reversible component of heat flow of the sample as a function of sample temperature. Curve 223 (FIG. 2c) is a plot of the rapidly reversible component of heat flow of the sample as a function of sample temperature. Curve 222 (FIG. 2c) is a plot of the combined heat flow, which is the sum of curve 221 and curve 223, as a function of sample temperature.

PET is a well understood material which produces three well-separated and easily observed heat flow transitions between 50° C. and 275° C. In the first transition, the sample passes from the vitreous state to the plastic state, resulting in an increase in the heat capacity of the sample. The first transition appears as feature 203 in FIG. 2a; feature 213 in FIG. 2b; and features 224, 227 and 230 in FIG. 2c. In the second transition, the sample passes from a more disorganized crystalline state to that of a more perfect crystal, giving off heat energy in the process. The second transition appears as feature 204 in FIG. 2a; feature 214 in FIG. 2c; and features 225, 228 and 231 in FIG. 2c. In the third transition, the sample passes from the solid state to the melted state. The third transition appears as feature 205 in FIG. 2a; feature 215 in FIG. 2c; and features 226, 229 and 232 in FIG. 2c.

The process of heating, quenching, reheating and slow cooling the PET sample freezes several strain effects into the crystal structure of the sample material. These strain effects appear as transitions which can be readily identified in the example curves. The first transition can be seen at approximately 75° C. as a small non-reversible endothermic peak over-lapped with a glass transition (baseline shift). This transition appears as part of feature 203 of curve 201 (FIG. 2a), and feature 227 of curve 222 (FIG. 2c). In FIG. 2c, it can be seen that the strain peak, feature 224 in curve 221, has been separated from the first transition, feature 227 of curve 222. In a similar fashion, the glass transition, feature 230 of curve 223, has been separated from the baseline shift due to the glass transition of curve 222.

The second transition can be seen at approximately 125° C. as a large non-reversible exothermic recrystallization peak in feature 204 of curve 201 (FIG. 2a), and feature 228 of curve 222 (FIG. 2c). In FIG. 2c, curve 221, it can be seen that the recrystallization peak, feature 225, has been separated from the combined heat flow curve, curve 222, and assigned almost completely to the non-rapidly reversible curve (curve 221) as feature 225. It is not presently understood whether the small rapidly reversible feature, 231, of curve 223 is an artifact of the deconvolution process or a small rapidly reversible component of the recrystallization process itself.

The third transition can be seen at approximately 250° C. as a large endothermic melt peak in feature 205 of curve 201 (FIG. 2a), and feature 229 of curve 222 (FIG. 2c). In FIG. 2c, curve 221, it can be seen that an initial exothermic crystal structure change, feature 233, is overlapped with a trailing endothermic event, feature 234, as the melt reaches completion. The initial exotherm is attributed to crystal structure reorganization just prior to the actual melting of the sample crystal. The trailing endotherm is not well understood but may be due in part to super-cooling of the melted sample as the sample temperature decreases momentarily during each modulation cycle. Feature 232 of curve 223 is a large endothermic melt peak.

The deconvoluted scan in FIG. 2c can be readily compared to the conventional scan in FIG. 2a. Both scans took the same amount of time to complete. However, when compared with the conventional DSC scan in FIG. 2a, the separation of overlapped rapidly reversible and non-rapidly reversible events in FIG. 2c provides the analyst with greater insight into the nature of the processes taking place at each transition.

EXAMPLE 3: EFFECT OF MODULATION FREQUENCY ON SEPARATION OF GLASS TRANSITION, RECRYSTALLIZATION AND MELTING EVENTS INTO RAPIDLY REVERSIBLE AND NON-RAPIDLY REVERSIBLE HEAT FLOW DATA

Figure 3A:
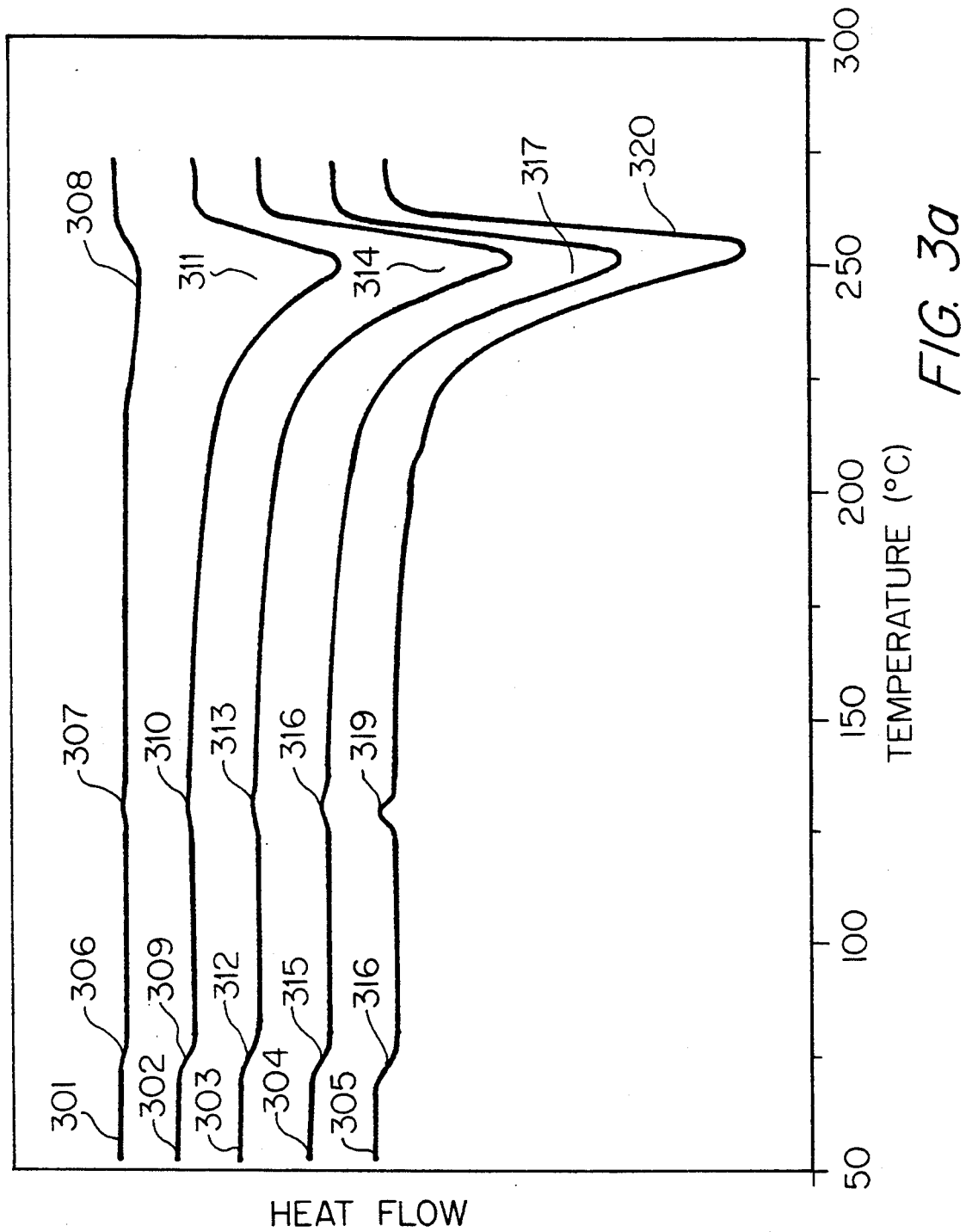
FIGS. 3a and 3b are DSC scans of Poly(ethylene terephthalate) (PET) obtained according to the methods described in Example 3.
Figure 3B:
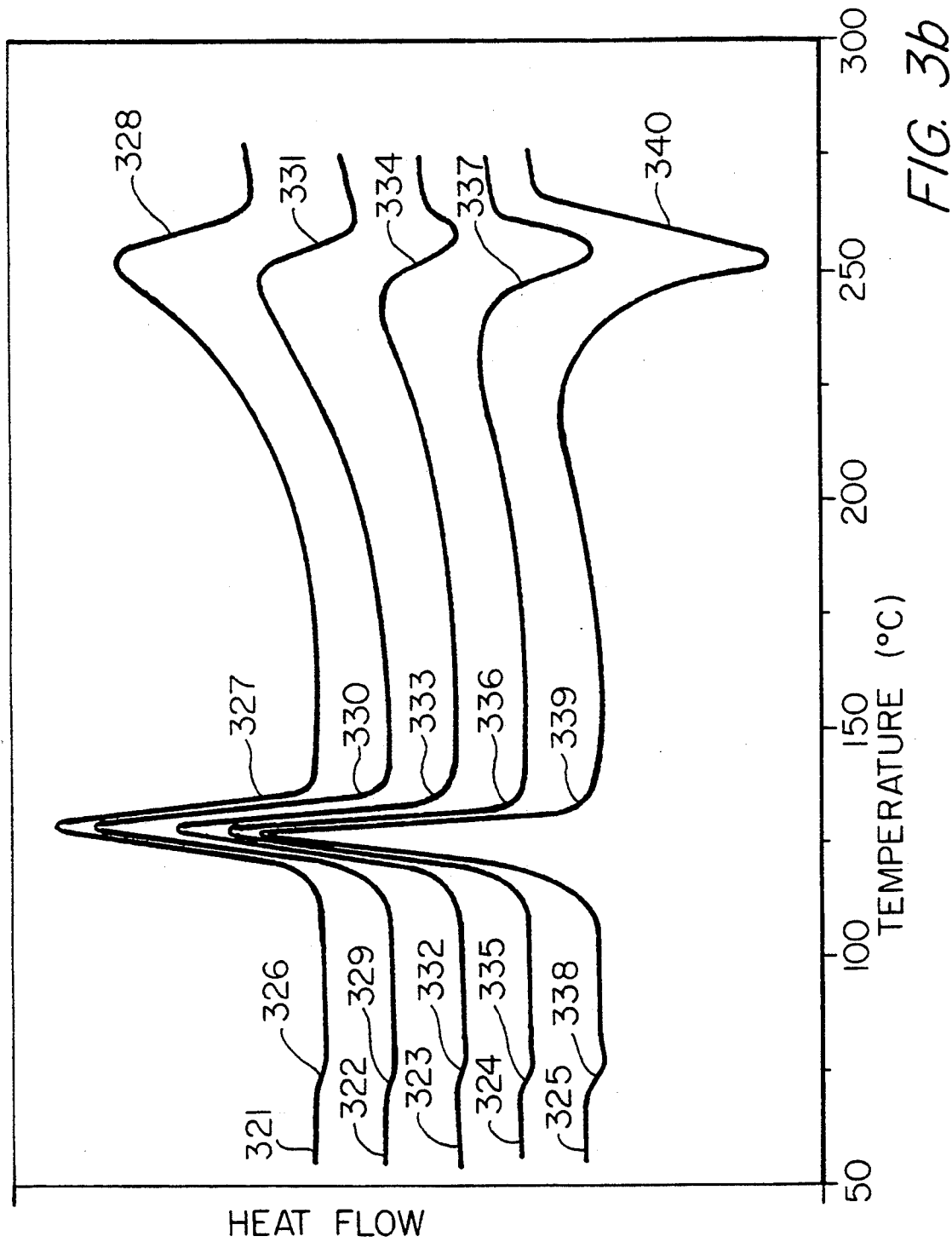

A 5.1 milligram sample of quenched Poly(ethylene teraphthalate) (PET) was examined by the method of the preferred embodiment of the present invention to compare the results obtained using different modulation frequencies. The experimental procedures followed in this example for setting up the apparatus, weighing the samples, loading the samples, and running analyses were described in Example 1. The sample was conditioned prior to each run by heating the sample to 300° C. in the DSC cell; removing the sample from the DSC cell and immediately quench-cooling it to 0° C. by placing the sample pan on a block of ice for 5 seconds. FIGS. 3a and 3b show representative DSC scans obtained according to the preferred embodiment (steps 1-8) of the present invention, at an underlying heating rate of 5° C./minute from ambient temperature to 300° C., using various modulation frequencies and approximately constant modulation amplitudes of +/−7.5° C./minute. Each curve has been normalized, corrected for baseline slope, and smoothed to remove ambient and instrument effects.

Each of the figures shows 5 curves. Curves 301, 302, 303, 304 and 305 (FIG. 3a) are plots of the rapidly reversible components of heat flow as a function of sample temperature. Curves 321, 322, 323, 324 and 325 (FIG. 3b) are plots of the non-rapidly reversible components of heat flow as a function of sample temperature. Curves 301, 302, 303, 304 and 305 correspond to modulation periods of 10, 20, 30, 40 and 50 seconds/cycle respectively. Curves 321, 322, 323, 324 and 325 correspond to modulation periods of 50, 40, 30, 20 and 10 seconds/cycle respectively. FIG. 3a shows the effect on rapidly reversible heat flow as the modulation frequency is varied from a cycle period of 10 seconds/cycle (curve 301) to a period of 50 seconds/cycle (curve 305). FIG. 3b shows the effect on non-rapidly reversible heat flow as the modulation frequency is varied from a cycle period of 50 seconds/cycle (curve 321) to a period of 10 seconds/cycle (curve 325).

As noted in Example 2, PET is a well understood material which produces three well separated and easily observed heat flow transitions between 50° C. and 275° C. The first transition appears as features 306, 309, 312, 315 and 318 in FIG. 3a, and as features 326, 329, 332, 335 and 338 in FIG. 3b. The second transition appears as features 307, 310, 313, 316 and 319 in FIG. 3a, and as features 327, 330, 333, 336 and 339 in FIG. 3b. The third transition appears as features 308, 311, 314, 317 and 320 in FIG. 3a, and as features 328, 331, 334, 337 and 340 in FIG. 3b.

FIG. 3a shows that increasing the modulation frequency decreases the magnitude of the rapidly reversible component of heat flow for each transition. The reason for this is not fully understood. It is believed, however, that this is because transitions are time as well as temperature dependent, and high frequency oscillations in heating rate do not allow sufficient time for the completion of reversible transitions. In each case the shape of the curve remains the same.

FIG. 3b shows that increasing the modulation frequency changes the shape of the non-rapidly reversible curve as well as affecting the size of the transition. The effect of changing frequency significantly changes the melt peak (features 328, 331, 334, 337 and 340), but has little affect on the recrystallization peak (features 327, 330, 333, 336 and 339). The reason for this is not fully understood. However, it is believed that this is because the recrystallization peak is irreversible, whereas the melt peak contains both reversible and non-reversible components. At high frequencies, the melted sample material super-cools, but at low frequencies it has sufficient time to recrystallize. As can be seen from the curves of FIGS. 3a and 3b, variation in the modulation frequency is a significant factor in controlling transition effects as measured by the method of the present invention.

EXAMPLE 4: EFFECT OF MODULATION AMPLITUDE ON SEPARATION OF GLASS TRANSITION, RECRYSTALLIZATION AND MELTING EVENTS INTO RAPIDLY REVERSIBLE AND NON-RAPIDLY REVERSIBLE HEAT FLOW DATA

Figure 4A:
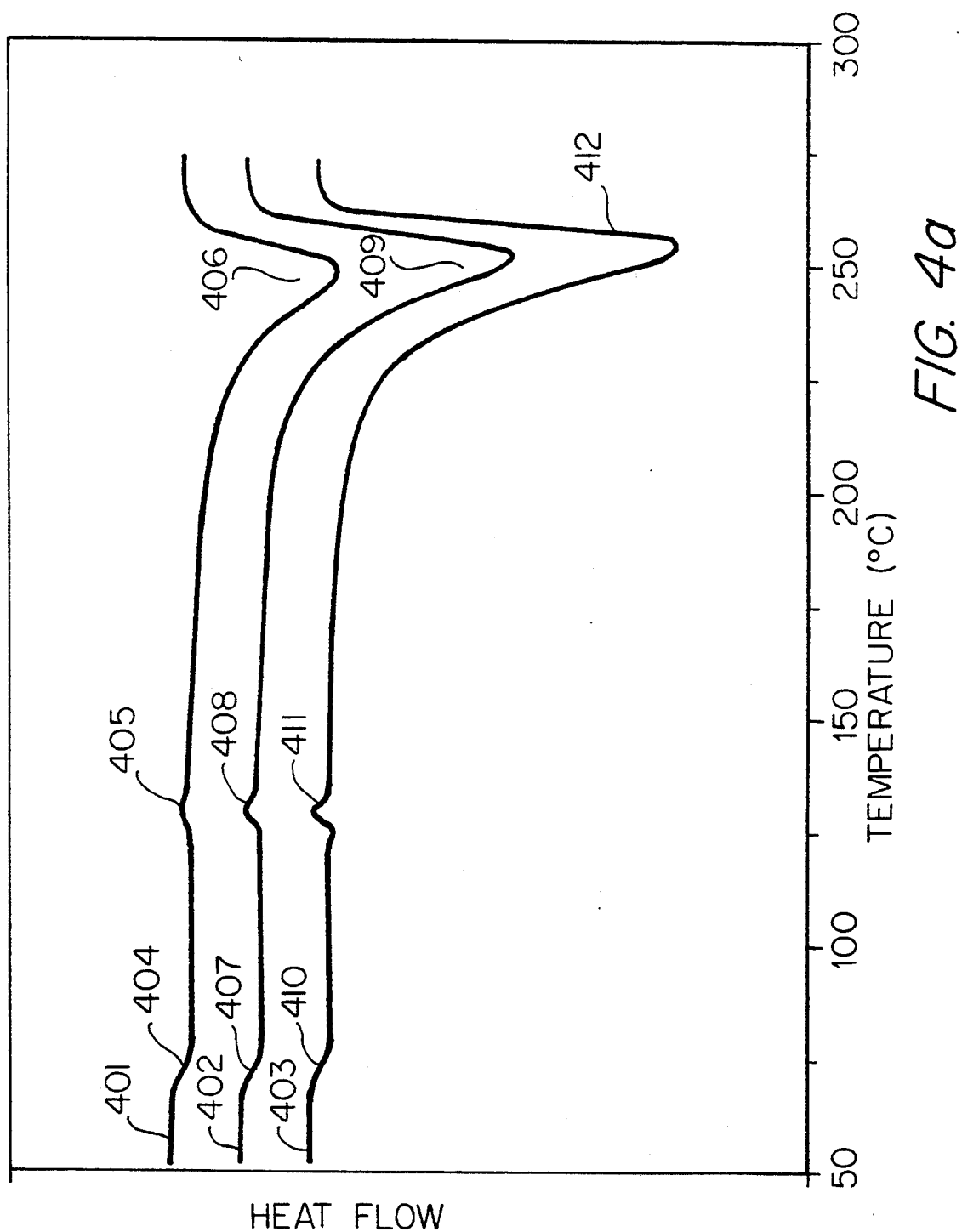
FIGS. 4a and 4b are DSC scans of Poly(ethylene terephthalate) (PET) obtained according to the methods described in Example 4.
Figure 4B:
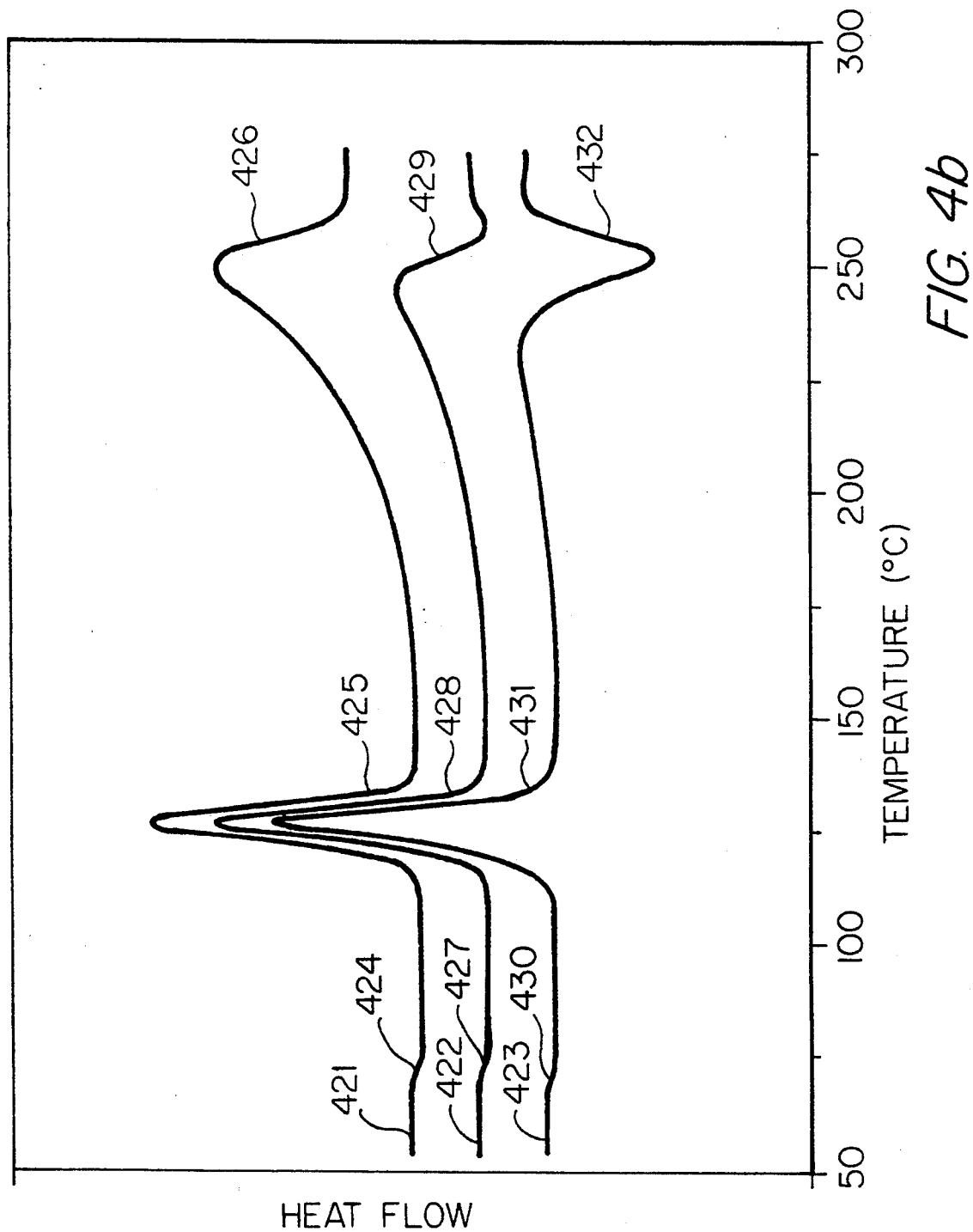

A 5.1 milligram sample of quenched Poly(ethylene teraphalate) (PET) was examined by the method of the preferred embodiment of the present invention to compare the results obtained using different modulation amplitudes. The experimental procedures followed in this example for setting up the apparatus, weighing the samples, loading the samples, and running analyses were described in Example 1. The sample was conditioned prior to each run by heating the sample to 300° C. in the DSC cell; removing the sample from the DSC cell and immediately quench cooling it to 0° C. by placing the sample pan on a block of ice for 5 seconds. FIGS. 4a and 4b show representative DSC scans obtained according to the preferred embodiment (steps 1-8) of the present invention, at an underlying heating rate of 5° C./minute from ambient temperature to 300° C., using various modulation amplitudes at a constant modulation period of 50 seconds/cycle. Each curve has been normalized, corrected for baseline slope, and smoothed to remove ambient and instrument effects.

Each of the figures shows 3 curves. Curves 401, 402 and 403 (FIG. 4a) are plots of the rapidly reversible component of heat flow as a function of sample temperature. Curves 421, 422 and 423 (FIG. 4b) are plots of the non-rapidly reversible components of heat flow as a function of sample temperature. Curves 401, 402 and 403 correspond to modulation amplitudes of +/−20°, +/−10° and +/−5° C./minute respectively, at a modulation period of 50 seconds/cycle. Curves 421, 422 and 423 correspond to modulation amplitudes of +/−5°, +/−10° and +/−20° C./minute respectively, at a modulation period of 50 seconds/cycle. FIG. 4a shows the effect of modulation amplitude on rapidly reversible heat flow as the modulation amplitude is varied by +/−20° C./minute (curve 401) to +/−5° C./minute (curve 403). FIG. 4b shows the effect on rapidly reversible heat flow as the modulation amplitude is varied by +/−5° C./minute (curve 421) to +/−20° C./minute (curve 423).

As noted above in Example 2, PET is a well understood material which produces three well separated and easily observed heat flow transitions between 50° C. and 275° C. The first transition appears as features 404, 407 and 410 in FIG. 4a, and as features 424, 427 and 430 in FIG. 4b. The second transition appears as features 405, 408 and 411 in FIG. 4a, and as features 425, 428 and 431 in FIG. 4b. The third transition appears as features 406, 409 and 412 in FIG. 4a, and as features 426, 429 and 432 in FIG. 4b.

FIGS. 4a and 4b show that increasing the modulation amplitude has little affect on the glass transition and recrystallization peak, but has a substantial affect on the melt peak. It is not fully understood why the various transitions change as they do. There is, however, substantial literature to support several theories. It is believed that the glass transition is largely unchanged because this transition is mostly time dependent. It is believed that the recrystallization peak is largely unchanged because this transition is irreversible. It is also believed that the melting transition is affected by a change in amplitude because the width of the temperature excursion on each cycle affects the tendency for super cooling versus recrystallization during the cooling portion of the modulation cycle. As can be seen from the curves of FIGS. 4a and 4b, variation in modulation amplitude is a significant factor in controlling transition effects as measured by the present invention.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method for analyzing a material using a differential scanning calorimeter comprising the steps of:
   (a) selecting an underlying heating rate, modulation frequency and modulation amplitude;
   (b) lacing a sample of the material in the differential scanning calorimeter;
   (c) varying the temperature of the sample in the differential scanning calorimeter according to the selected underlying heating rate, the selected modulation frequency and the selected modulation amplitude;
   (d) recording a signal representative of differential changes in the heat flow to and from the sample; and
   (e) deconvoluting the signal representative of differential changes in the heat flow to and from the sample to compute at least one deconvoluted signal.

2. The method of claim 1, wherein the step of deconvoluting the signal representative of differential changes in the heat flow to and from the sample to compute at least one deconvoluted signal comprises deconvoluting the signal into rapidly reversible and non-rapidly reversible components.

3. The method of claim 2, further comprising the step of adjusting the frequency of the modulation of the temperature according to the at least one deconvoluted signal.

4. The method of claim 2, further comprising the step of adjusting the amplitude of the modulation of the temperature according to the at least one deconvoluted signal.

5. The method of claim 2, further comprising the step of controlling the underlying heating rate according to the at least one deconvoluted signal.

6. A method for analyzing a material using a differential thermal analyzer comprising the steps of:
   (a) selecting an underlying heating rate, modulation frequency and modulation amplitude;
   (b) placing a sample of the material in a differential thermal analyzer;
   (c) varying the temperature of the sample in the differential thermal analyzer according to the selected underlying heating rate, the selected modulation frequency and the selected modulation amplitude;
   (d) recording a signal representative of differential changes in the heat flow to and from the sample; and
   (e) deconvoluting the signal representative of differential changes in the heat flow to and from the sample to compute at least one deconvoluted signal.

7. The method of claim 6, wherein the step of deconvoluting the signal representative of differential changes in the heat flow to and from the sample to compute at least one deconvoluted signal comprises deconvoluting the signal into rapidly reversible and non-rapidly reversible components.

8. The method of claim 7, further comprising the step of adjusting the frequency of the modulation of the temperature according to the at least one deconvoluted signal.

9. The method of claim 7, further comprising the step of adjusting the amplitude of the modulation of the temperature according to the at least one deconvoluted signal.

10. The method of claim 7, further comprising the step of controlling the underlying heating rate according to the at least one deconvoluted signal.

11. A differential scanning calorimeter comprising:
    (a) means for varying the temperature of a sample in the differential scanning calorimeter according to an underlying heating rate;

(b) means for selecting a modulation frequency and a modulation amplitude;

(c) means for controlling the temperature of the sample according to the selected underlying heating rate, modulation frequency and modulation amplitude;

(d) means for detecting the heat flow to and from the sample with respect to a reference as a function of temperature, as the temperature is varied according to the modulation frequency and the modulation amplitude;

(e) means for recording a signal representative of differential changes in the heat flow to and from the sample; and (f) means for deconvoluting the signal representative of differential changes in the heat flow to and from the sample to compute at least one deconvoluted signal.

12. The differential scanning calorimeter of claim 11, wherein the means for deconvoluting the signal representative of differential changes in the heat flow to and from the sample to compute at least one deconvoluted signal comprises means for deconvoluting the signal into rapidly reversible and non-rapidly reversible components.

13. The differential scanning calorimeter of claim 12, further comprising means for adjusting the frequency of the modulation of the temperature according to the at least one deconvoluted signal.

14. The differential scanning calorimeter of claim 12, further comprising means for adjusting the amplitude of the modulation of the temperature according to the at least one deconvoluted signal.

15. The differential scanning calorimeter of claim 12, further comprising means for controlling the underlying heating rate according to the at least one deconvoluted signal.

16. A differential thermal analyzer comprising:

(a) means for varying the temperature of a sample in the differential thermal analyzer according to an underlying heating rate;

(b) means for selecting a modulation frequency and a modulation amplitude;

(c) means for controlling the temperature of the sample according to the selected underlying heating rate, modulation frequency and modulation amplitude;

(d) means for detecting the heat flow to and from the sample with respect to a reference as a function of temperature, as the temperature is varied according to the modulation frequency and the modulation amplitude;

(e) means for recording a signal representative of differential changes in the heat flow to and from the sample; and (f) means for deconvoluting the signal representative of differential changes in the heat flow to and from the sample to compute at least one deconvoluted signal.

17. The differential thermal analyzer of claim 16, wherein the means for deconvoluting the signal representative of differential changes in the heat flow to and from the sample to compute at least one deconvoluted signal comprises means for deconvoluting the signal representative of differential changes in the heat flow to and from the sample into rapidly reversible and non-rapidly reversible components.

18. The differential thermal analyzer of claim 17, further comprising means for adjusting the frequency of the modulation of the temperature according to the at least one deconvoluted signal.

19. The differential thermal analyzer of claim 17, further comprising means for adjusting the amplitude of the modulation of the temperature according to the at least one deconvoluted signal.

20. The differential thermal analyzer of claim 17, further comprising means for controlling the underlying heating rate according to the at least one deconvoluted signal.

21. A method for analyzing a material comprising the steps of:

(a) placing a sample of the material in an apparatus for detecting differential changes in the heat flow to a sample material with respect to a reference, as a function of temperature;

(b) varying the temperature at an underlying heating rate modulated by a modulation function, said modulation function having a preselected modulation frequency and a preselected modulation amplitude;

(c) monitoring a differential signal representative of the differential change in the heat flow to the sample material with respect to the reference;

(d) recording the differential signal representative of the differential change in the heat flow to the sample material with respect to the reference; and (e) deconvoluting the signal representative of the differential change in the heat flow to the sample material with respect to the reference to compute at least one deconvoluted signal.

22. The method of claim 21, wherein the step of deconvoluting the signal representative of the differential change in the heat flow to the sample material with respect to the reference to compute at least one deconvoluted signal comprises deconvoluting the signal representative of the differential change in the heat flow to the sample material with respect to the reference, into rapidly reversing, and non-rapidly reversing components.

23. The method of claim 21, wherein the modulation function is a sinusoidal oscillation.

24. The method of claim 21, wherein the modulation function is a combination of at least two sinusoidal oscillations.

25. The method of claim 21, wherein the modulation function is selected from the group of modulation functions consisting of square waves, sawtooth waves, triangular waves, pulse waves, polynomial waves, and combinations thereof.

26. The method of claim 21, further comprising the step of deconvoluting the signal representative of the differential change in the heat flow to the sample material with respect to the reference, using a discrete Fourier transform.

27. The method of claim 26, wherein the signal representative of differential changes in the heat flow to and from the sample is differential temperature.

28. The method of claim 21, wherein the differential signal representative of the differential change in the heat flow to the sample material with respect to the reference, is differential temperature.

29. A thermal analysis instrument comprising:

(a) a furnace comprising a heater, a heater controller, and a furnace chamber;

(b) a sample pan and a reference pan in the furnace chamber;

(c) means for monitoring the temperature of the sample pan and the temperature difference between the sample pan and the reference pan;

(d) means for controlling the temperature of the furnace chamber;

(e) means for receiving a signal representative of the temperature of the sample pan and of the temperature difference between the sample pan and the reference pan, for calculating a signal representative of differential changes in heat flow to the sample pan with respect to heat flow to the reference pan from the signal representative of the temperature of the sample pan and of the temperature difference between the sample pan and the reference pan, and for controlling the means for controlling the temperature of the furnace chamber;

(f) means for (i) selecting an underlying heating rate for the furnace chamber, (ii) selecting a modulation frequency and a modulation amplitude, and (iii) controlling the temperature of the sample pan according to the selected underlying heating, modulation frequency and modulation amplitude;

(g) means for recording the signal representative of differential changes in the heat flow to the sample pan with respect to the heat flow to the reference pan; and (h) means for deconvoluting the signal representative of differential changes in the heat flow to the sample pan with respect to the heat flow to the reference pan to compute at least one deconvoluted signal.

30. The thermal analysis instrument of claim 29, wherein the means for deconvoluting the signal representative of differential changes in the heat flow to the sample pan with respect to the heat flow to the reference pan to compute at least one deconvoluted signal comprises means for deconvoluting the signal representative of differential changes in the heat flow to the sample pan with respect to the heat flow to the reference pan into rapidly reversible an non-rapidly reversible components.

31. The thermal analysis instrument of claim 30, wherein the means for deconvoluting the signal representative of differential changes in the heat flow to the sample pan with respect to the heat flow to the reference pan into rapidly reversible and non-rapidly reversible components uses a discrete differential Fourier transform technique.

32. The thermal analysis instrument of claim 29, wherein the sample pan and the reference pan are on a support in the furnace chamber, and wherein the support serves as the major heat flow path for transferring heat from the furnace to the sample pan and to the reference pan.

33. A thermal analysis instrument comprising:
(a) a sample position and a reference position;
(b) means for heating a sample placed at the sample position and a reference placed at the reference position;
(c) means for monitoring the heat flow to the sample and the heat flow to the reference;
(d) means for receiving a signal representative of the heat flow to the sample and the heat flow to the reference;

(e) means for recording the signal representative of the heat flow to the sample and the heat flow to the reference;

(f) means for selecting an underlying heating rate, modulation frequency and modulation amplitude;

(g) means for controlling the temperature of the sample according to the selected underlying heating rate, modulation frequency and modulation amplitude;

(h) means for calculating a signal representative of differential changes in the heat flow to the sample with respect to the heat flow to the reference; and (i) means for deconvoluting the signal representative of differential changes in the heat flow to the sample with respect to the heat flow to the reference to compute at least one deconvoluted signal.

34. The thermal analysis instrument of claim 33, wherein the means for deconvoluting the signal representative of differential changes in the heat flow to the sample with respect to the heat flow to the reference to compute at least one deconvoluted signal comprises means for deconvoluting the signal representative of differential changes in the heat flow to the sample with respect to the heat flow to the reference into rapidly reversible and non-rapidly reversible components.

35. The thermal analysis instrument of claim 34, wherein the means for deconvoluting the signal representative of differential changes in the heat flow to the sample with respect to the heat flow to the reference into rapidly reversible and non-rapidly reversible components uses a discrete differential Fourier transform technique.

36. The thermal analysis instrument of claim 33, wherein the sample and the reference are on a support, and wherein the support serves as the major heat flow path for heat transfer.

37. A method for analyzing a material using a differential scanning calorimeter comprising the steps of:
(a) selecting an underlying heating rate, modulation frequency and modulation amplitude;
(b) placing a sample of the material in the differential scanning calorimeter;
(c) varying the temperature of the sample in the differential scanning calorimeter according to the selected underlying heating rate, the selected modulation frequency and the selected modulation amplitude;
(d) recording a signal representative of differential changes in the heat flow to and from the sample; and
(e) deconvoluting the signal representative of differential changes in the heat flow to and from the sample to compute two deconvoluted signals.

38. The method of claim 37, wherein the step of deconvoluting the signal representative of differential changes in the heat flow to and from the sample to compute two deconvoluted signals comprises deconvoluting the signal into a rapidly reversible component and a non-rapidly reversible component.

39. A method for analyzing a material using a differential thermal analyzer comprising the steps of:
(a) selecting an underlying heating rate, modulation frequency and modulation amplitude;
(b) placing a sample of the material in a differential thermal analyzer;
(c) varying the temperature of the sample in the differential thermal analyzer according to the selected underlying heating rate, the selected modulation frequency and the selected modulation amplitude;

(d) recording a signal representative of differential changes in the heat flow to and from the sample; and (e) deconvoluting the signal representative of differential changes in the heat flow to and from the sample to compute two deconvoluted signals.

40. The method of claim 39, wherein the step of deconvoluting the signal representative of differential changes in the heat flow to and from the sample to compute two deconvoluted signals comprises deconvoluting the signal into a rapidly reversible component and a non-rapidly reversible component.

41. A differential scanning calorimeter comprising:

(a) means for varying the temperature of a sample in the differential scanning calorimeter according to an underlying heating rate;

(b) means for selecting a modulation frequency and a modulation amplitude;

(c) means for controlling the temperature of the sample according to the selected underlying heating rate, modulation frequency and modulation amplitude;

(d) means for detecting the heat flow to and from the sample with respect to a reference as a function of temperature, as the temperature is varied according to the modulation frequency and the modulation amplitude;

(e) means for recording a signal representative of differential changes in the heat flow to and from the sample; and (f) means for deconvoluting the signal representative of differential changes in the heat flow to and from the sample to compute two deconvoluted signals.

42. The differential scanning calorimeter of claim 41, wherein the means for deconvoluting the signal representative of differential changes in the heat flow to and from the sample to compute two deconvoluted signals comprises means for deconvoluting the signal into a rapidly reversible component and a non-rapidly reversible component.

43. A differential thermal analyzer comprising:

(a) means for varying the temperature of a sample in the differential thermal analyzer according to an underlying heating rate;

(b) means for selecting a modulation frequency and a modulation amplitude;

(c) means for controlling the temperature of the sample according to the selected underlying heating rate, modulation frequency and modulation amplitude;

(d) means for detecting the heat flow to and from the sample with respect to a reference as a function of temperature, as the temperature is varied according to the modulation frequency and the modulation amplitude;

(e) means for recording a signal representative of differential changes in the heat flow to and from the sample; and (f) means for deconvoluting the signal representative of differential changes in the heat flow to and from the sample to compute two deconvoluted signals.

44. The differential thermal analyzer of claim 43, wherein the means for deconvoluting the signal representative of differential changes in the heat flow to and from the sample to compute two deconvoluted signals comprises means for deconvoluting the signal representative of differential changes in the heat flow to and from the sample into a rapidly reversible component and a non-rapidly reversible component.

* * * * *

UNITED STATES PATENT AND TRADEMARK OFFICE
CERTIFICATE OF CORRECTION

PATENT NO. : 5,346,306

DATED : September 13, 1994

INVENTOR(S) : Reading et al.

It is certified that error appears in the above-indentified patent and that said Letters Patent is hereby corrected as shown below:

Column 15, line 67, claim 1, please delete "lacing" and insert --placing-- therefor.

Column 19, line 23, claim 29, Paragraph (f), please insert --rate-- after "heating."

Signed and Sealed this

Seventh Day of February, 1995

Attest:

BRUCE LEHMAN

Attesting Officer

Commissioner of Patents and Trademarks

(12) REEXAMINATION CERTIFICATE (4567th)
United States Patent
Reading et al.

(10) Number: US 5,346,306 C1
(45) Certificate Issued: *May 7, 2002

(54) METHOD AND APPARATUS FOR MODULATED DIFFERENTIAL ANALYSIS

(75) Inventors: Michael Reading, London (GB); Brian K. Hahn, Newark; Benjamin S. Crowe, Centerville, both of DE (US)

(73) Assignee: TA Instruments, Inc., New Castle, DE (US)

Reexamination Request:
No. 90/005,517, Oct. 12, 1999
No. 90/005,770, Jul. 14, 2000

Reexamination Certificate for:
Patent No.: 5,346,306
Issued: Sep. 13, 1994
Appl. No.: 08/060,214
Filed: May 7, 1993

(*) Notice: This patent is subject to a terminal disclaimer.

Certificate of Correction issued Feb. 7, 1995.

Related U.S. Application Data

(63) Continuation of application No. 07/844,448, filed on Mar. 2, 1992, now Pat. No. 5,224,775.

(51) Int. Cl.$^7$ .............................................. G01N 25/00

(52) U.S. Cl. .............................. 374/10; 374/22; 374/43

(58) Field of Search .............................. 374/10, 11, 12, 374/13, 14, 16, 31, 33, 43

(56) References Cited

U.S. PATENT DOCUMENTS 5,080,495 A   1/1992   Hashimoto et al.

OTHER PUBLICATIONS

*Computerized Equipment For Measuring The Amplitude And Phase Of ULF Harmonic Signals*, Plenum Publishing Corporation, 1987, pp. 763–767.

Physical Review Letters, First–Order Transition in Chromium at the Neel Temperature, P.R. Garnier and M.B. Salamon, Oct. 13, 1971, pp. 1523–1526.

S.C. Mraw and D.F. Naas, "The Measurement of Accurate Heat Capacities by Differential Scanning Calorimetry: Comparison of d.s.c. Results of Pyrite (100 to 800 K) with Literature Values from Precision Adiabatic Calorimetry," J. Chem. Thermodynamics, vol. 11, 1979, pp. 567–584.

P. Claudy, J.C. Commeron, and J.M. Letoffe, "Quasi–Study of the Glass Transition of Glycerol by DSC," Thermochimica Acta, vol. 128, Aug. 1988, pp. 251–260.

A. Maesono and R. Kato, translation into English of a Japanese article, "Recently Developed Instruments Relevant to ac Calorimetry."

H. Albert, "Pulsed–Current Control and Measurement System for Precision Microcalorimetry," The Review of Scientific Instruments, vol. 43, No. 5, 1972, pp. 766–774.

J. Zynger, "Automated, Stepping Differential Calorimeter for the Analysis of Purity," Analytical Chemistry, vol. 47, No. 8, Jul. 1975, pp. 1380–1384.

T. Sturgill, R. Johnson, and R. Biltonen, "Thermal Perturbation Techniques in Characterizing Ligand–Macromolecule Interactions: Theory and Application to the Proflavin–a–Chymotrypsin System," Biopolymers, vol. 17, 1978, pp. 1773–1792.

P. Privalov, "Scanning Microcalormeters for Studying Macromolecules," Pure & Appl. Chem., vol. 52, 1980, pp. 479–497.

(List continued on next page.)

*Primary Examiner*—G. Bradley Bennett

(57) ABSTRACT

The present invention relates to differential analytical techniques for determining the composition, phase, structure, identification or other properties of a material that undergoes a transition as function of a driving variable. As applied to differential scanning calorimetric analysis (DSC), the preferred embodiment comprises: (1) heating a sample of the material with a linear temperature ramp that is modulated with a sinusoidal heating rate oscillation; and (2) deconvoluting the resultant heat flow signal into rapidly reversible and non-rapidly reversible components.

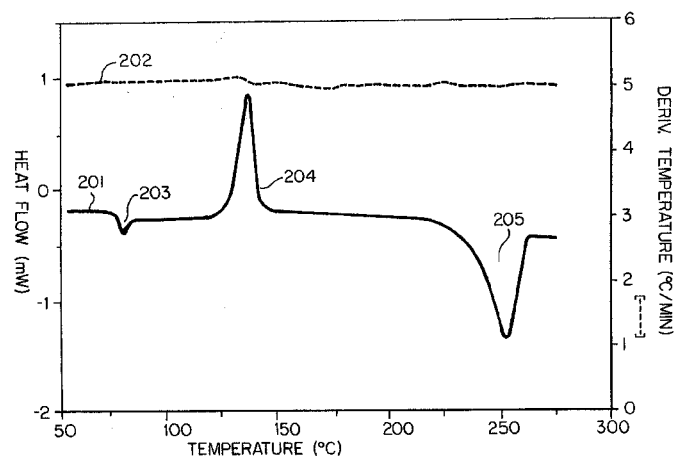

OTHER PUBLICATIONS

C. Festa and N. Ceccanti, "A Differential Calorimeter for Measuring Heats of Solution With a Pulse Time Modulation System," Societa Chimica Italiana, 1980, pp. 431–437.

W. Van Osdol, R. Biltonen, and M. Johnson, "Measuring the Kinetics of Membrane Phase Transitions," Journal of Biochemical and Biophysical Methods, vol. 20, 1989, pp. 1–46.

J. Rouquerol, "Controlled Transformation Rate Thermal Analysis: The Hidden Face of Thermal Analysis," Thermochimica Acta, 144, 1989, pp. 209–224.

D. Cahill, "Thermal Conductivity Measurement from 30 to 750 K the 3u Method," Rev. Sci. Instrum. vol. 62, Feb. 1990, pp. 802–808.

D. Bertolini, M. Cassettari, G. Salvetti, E. Tombari, and S. Veronesi, "A Differential Calorimetric Technique for Heat Capacity and Thermal Conductivity Measurement of Liquids," Rev. Sci. Instrum., vol. 61, No. 9, Sep. 1990, pp. 2416–2419.

A.M. Cocero and J.L. Kokini, "The Study of the Glass Transition of Glutenin Using Small Amplitude Oscillatory Rheological Measurements and Differential Scanning Calorimetry," The Society of Rheology, Inc. vol. 35, No. 2, Feb. 1991, pp. 257–270.

M. Barrio, J. Font, J. Montasell, and J. Ll. Tamarit, "AC Calorimetry Applied To Powdered Samples, Simulation and Tests," Journal of Thermal Analysis, vol. 37, 1991, pp. 39–52.

Y. Saruyama, "AC Calorimetry at the First Order Phase Transition Point," Journal of Thermal Analysis, vol. 38, 1992, pp. 1827–1833.

Y.A. Kraftmakher, "Modulation Calorimetry," Institute of Inorganic Chemistry, pp. 591–641.

M. Straume and E. Freire, "Two–Dimensional Differential Scanning Calorimetry: Simultaneous Revolution of Intrinsic Protein Structurel Energetic And Ligand Binding Interactions by Global Linkage Analysis," Analytical Biochemistry, 203, 1992, pp. 259–268.

C.W. Garland, "High–Resolution AC Calorimetry and Critical Behavior at Phase Transitions," Thermochimica Acta 88 (1985) pp. 127–142.

M. Meichle and C.W. Garland, "Calorimetric study of the smectic–A—smectic–C phase transition in liquid crystals," Physical Review A, 27 (5), May, 1983, pp. 2624–2631.

G. Sanchez, M. Meichle and C.W. Garland, "Critical heat capacity in a 3–methylpentane + nitroethane mixture near its consolute point," Physical Review A, 28(8), Sep., 1983.

S. Ikeda and Y. Ishikawa, "Improvement of AC Calorimetry," Japanese Journal of Applied Physics, 18 (7), Jul. 1979, pp. 1367–1372.

S. Imaizumi, T. Matsuda, and I. Hatta, "Measurement of Dynamic Specific Heat Capacity of Lysozome Crystals," Journal of the Physical Society of Japan, 47 (5), Nov., 1979.

J. Ohsawa, T. Nishinaga and S. Uchiyama, "Measurement of the Specific Heat of Boron Monophosphide by AC Calorimetry," Japanese Journal of Applied Physics, 17 (6), Jun., 1978.

J.E. Smaardyk and J.M. Mochel, "High resolution ac calorimeter for organic liquids," Review of Scientific Instruments 49 (7), Jul. 1978, pp. 988–993.

"Complex Plane Analysis of Heat Capacity of Polymers in the Glass Transition Region," by H. Gobrecht et al., Journal of Physics E: Scientific Instruments, 1971, vol. 4, pp. 21–23.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–44 is confirmed.

\* \* \* \* \*